United States Patent [19]

Camprasse et al.

[11] Patent Number: 5,755,787
[45] Date of Patent: May 26, 1998

[54] SEMI-SYNTHETIC MATERIAL USABLE IN MEDICINE AND SURGERY

[75] Inventors: Georges Camprasse, Villenauxe la Petite; Serge Camprasse, Chelles, both of France

[73] Assignee: Pearl Ventures, Inc., Ridgefield, Conn.

[21] Appl. No.: 492,074

[22] PCT Filed: Feb. 4, 1994

[86] PCT No.: PCT/FR94/00135

§ 371 Date: Sep. 15, 1995

§ 102(e) Date: Sep. 15, 1995

[87] PCT Pub. No.: WO94/17838

PCT Pub. Date: Aug. 18, 1994

[30] Foreign Application Priority Data

Feb. 5, 1993 [FR] France ..................... 93 01387

[51] Int. Cl.$^6$ ..................... A61F 2/02
[52] U.S. Cl. ..................... 623/11; 623/16
[58] Field of Search ..................... 623/1, 11, 15, 623/16; 424/422, 423

[56] References Cited

FOREIGN PATENT DOCUMENTS

| | | |
|---|---|---|
| 0532421 | 3/1993 | European Pat. Off. . |
| 2637502 | 4/1990 | France . |
| 9014111 | 11/1990 | WIPO . |

OTHER PUBLICATIONS

Comptes Rendus De L'Academie des Sciences. vol. 309. No. 6. 27 Jul. 1989. pp. 203–210. Evelynè Lopez et al.

*Primary Examiner*—John G. Weiss
*Assistant Examiner*—John M. Black
*Attorney, Agent, or Firm*—Larson & Taylor

[57] ABSTRACT

A semi-synthetic material for producing shaped elements for use in orthopaedic surgery, bone stabilizing and regenerating materials and biological cement, made from the mother-of-pearl of aquatic molluscs which is subjected to a specific mechanical, thermal or chemical treatment in order to alter its physical and chemical structure. The material may be powdered, mixed with calcium hydroxide, any other calcium salt, collagen or starch, dried and shaped into prosthetic members. Said material may be combined with methyl or acrylic derivatives, antibiotics or antimitotic agents, and is suitable for use in orthopaedic surgery, dentistry, carcinology, ear, nose and throat medicine, gynaecology and ophthalmology.

9 Claims, No Drawings

SEMI-SYNTHETIC MATERIAL USABLE IN MEDICINE AND SURGERY

BACKGROUND OF THE INVENTION

1. Field of the Invention

The present invention relates to a semi-synthetic product obtained after a specific mechanical, thermal and chemical treatment of mother of pearl intended to modify the structure and the properties in such a manner that it may be used for the manufacture of shaped parts for the orthopaedic, craniofacial surgery, for the preparation of biological cements for the sealing of prostheses, of a bone regenerating material and of a stabilizing material in carcinology and in intervening imagery.

2. Description of the Related Art

The basic material, mother of pearl, originates from the nacreous test of aquatic mollusca, the physical-chemical structure of which comprises in addition to a mineral fraction representing 90% to 98% of the total mass in the shape of biocrystals, an organic fraction composed of fibers and non fibers, soluble or non-soluble proteins having a genic specificity making its use unsuitable in the actual state on the animal and on the man.

In effect, the biomaterial used as such would behave as a xenograft and would exhibit within a variable time its antigenic character with an unfavourable immunological reaction which could cause the rejection thereof.

SUMMARY OF THE INVENTION

One has found a mechanical, thermal and chemical process which permits to render insoluble the soluble fraction of the proteins, to tan the superficial portion and to prevent the tissual rejection phenomena.

DESCRIPTION OF THE PREFERRED EMBODIMENTS

Preferably the mother of pearl originates from the nacreous test of aquatic mollusca, bivalves, cephalopods and gasteropoda such as the Pinctada (Maxima, Margaritifera), the Concha, the Whelk, the Nautilus, the Ormer Tricdane, Triton Shell or any other mollusca the test of which contains the mother of pearl.

The specific treatment of the product according to the invention is composed in the following manner:

after the mechanical preparation of the shell of the mollusca, in order to obtain the nacreous portion alone, the latter is caused to be dipped for 24 hours in a bath of demineralized water containing 20% of hypochlorite. After washing under a water stream for 48 hours, the mother of pearl is caused to boil in a bath of demineralized water containing 20% of sodium hypochlorite for two 2 hours after change of the bath at each operation. At the end of these two steps, the material is rinsed with boiling water and placed in a drying oven where it undergoes a treatment with demineralized steam under a pressure of 2 bars for two 2 hour periods in the presence of chemical agents, the action of which is intended to fix and to tan the organic fraction and to cause a chemical surface reaction not only with the organic fraction but also with the mineral fraction. The agents for example are, without the list being limiting: sodium hypochlorite, acetic acid, glutaraldehyde, benzalkonium chloride, formaldehyde, diluted to 20%.

At the end of these steps, the product according to the invention is processed with demineralized steam under a pressure of 2 bars for one hour without any addition of chemical products. The product according to the invention is dried under vacuum by thermal stages up to 100°.

From now on the material according to the invention may be sterilized by gamma radiation at 2.5 megarads and is ready for use.

In order to modify the functional properties of the material in the powdery or plastic shape, one may add thereto mineral compounds such as: calcium hydroxide, calcium phosphate, calcium chloride or any other calcium salt, the product according to the invention in its powdery or plastic form then possesses adhesive properties which make it apt to be associated with other materials, such as, for instance, metals, and plastics materials.

The product according to the invention may also be associated with monomers or polymers as well as with methylic or acrylic derivatives.

The product according to the invention in its compact as well as powdery form may be impregnated under pressure with medicinal products which fix themselves upon the organic fraction of the mother of pearl and intended to be released again "in situ" at therapeutical doses for a determined time for the treatment of certain diseases affecting the bony tissue as well as the hollow organs.

In a preferred embodiment, the product according to the invention is used as a birth control coil impregnated with medicinal substances for the treatment of uterine diseases or with contraceptive substances.

The product according to the invention may serve as a support for a crystalline lens graft after the epithelialization of its surface underneath the jugal mucosa.

It may be machined to the shape of elements of substitution for the chain of ossicles of the middle ear.

One knows that during the physical-chemical treatment of the mother of pearl, there occurs therein a certain number of chemical surface reactions.

The surface product obtained is a stable precipitate characterizing the product according to the invention.

When the product according to the invention is placed in the bony tissue there occurs among others, under the effect of osmotic pressure and in the presence of the blood gases, in particular the $CO_2$ and oxygen $O_2$, the following chemical reaction

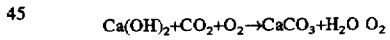
$$Ca(OH)_2 + CO_2 + O_2 \rightarrow CaCO_3 + H_2O\ O_2$$

This reaction resulting from the functional properties of the material according to the invention and being derived from the treatment of the latter explains in part the bioactive properties of the product according to the invention.

The product according to the invention may be used alone or associated with antimitotics and/or antibiotics and inserted or injected with the assistance of vectors into cavities or losses of bony substances of carcinological origins in order to consolidate the structure thereof and to stabilize the evolution thereof.

According to a preferred embodiment, the product according to the invention in its compact form or in its powdery form associated with monomers or polymers may be used as an embolism material in the tumors of vascular origins such as naevus, hemangiomas without this list being limiting.

The product according to the invention may be used in its powdery form as a consolidation material in the geodes of the femoral head and the degenerative diseases of the rachis.

The following example illustrates the behaviour of the material according to the invention used in surgery. 10 mm long cylindrical implants with a diameter of 4 mm have been placed into adequate cavities located in the femur of the beagle dog. A first set of implants have been made from decontaminated and sterilized mother of pearl, and a second set of implants have been made from the material according to the invention obtained after a specific treatment.

In the first cases one has observed within the variable periods which did not exceed 30 days, immunological reactions which have led to the expulsion of all the implants.

In the second case for all the implants made from the material according to the invention, one has radiologically noticed the absence of any radioclear zone between the receiving bone and the implants and clinically a perfect osteointegration between the receiving bones and the implants materialized by a rigidity of the latter, histologically by the exhibition of a brazing existing at the bone-implant interface.

One may consider as being particularly interesting the behaviour of the material according to the invention which in the compact form brings about a physical-chemical fusion with the receiving bone and once the osteointegration has been completed, undergoes no structural alteration with time whereas in the powdery plastic or combined form, it not only exhibits properties of adhesiveness to the bone or the metals or any other materials but also hemostatic and eutrophic properties materialized by a termination of hemorrhagic suffusions upon its being put in place on the operative site and an accelerated mucous cicatrization. It moreover causes local enzymatic reactions which lead to its total transformation into bony tissue.

The following descriptions illustrate the use of the material according to the invention without these examples being limiting ; it behoves the man skilled in the art to put the material according to the invention in use every time he will need orthopaedic prostheses or a biological cement or any other utilizations in animal and human surgery or medicine.

The material according to the invention in its compact form may take the shape of a tibial plate, of a femoral condyle, of a cotyloidal cavity, of the hip-joint, of a humeral head, of an iliae wing, of a bone of the skull-cap, of a screw. It may in its powdery form combined with the collagen or others and dried constitute pegs for intervertebral fusion, wedges for opening osteotomy, intersomatic blocks, plugs for cavities of bony, cystic or tumoral trepanning.

The following example illustrates the use of the product according to the invention in the form of a sealing biological cement in the case of a complete arthroplasty of the hip.

For more than 20 years, the hip prostheses are sealed with surgical cements the most frequently used of which is the methyl methacrylate, a plastic material which upon hardening provides an anchoring between the metal and the bony cortical of the femur into which the prosthesis is implanted. More recently one has proposed metallic prostheses designed so as to provide a biological anchoring without any cement. In the case of acrylic cements, several authors have drawn attention to the inconveniences of the latter: diffusion of the monomer into the circulation, poor mechanical properties, lack of elasticity, aging. But the major inconvenience resides in the fact that hardening which occurs upon setting is accompanied by an exothermic chemical reaction causing in a non-negligible number of cases a bony necrosis affecting the femoral cortical, which leads to the mobility of the prosthesis increased by an infectious risk necessitating the eradication of the cement and a renewal arthroplasty.

The material according to the invention in its powdery form has been used during a complete arthroplasty of the virgin hip on account of a coxitis with the fitting of a prosthesis with a trochanter-diaphysis bearing. The sealing cement is extemporaneously made with 20 g of the product according to the invention in its powdery form to which one adds in a fractionated manner whole blood from the patient so as to obtain a paste with a creamy consistency. The femur is prepared by resection of the head at the base of the neck above the lesser trochanter internally plumb with the greater trochanter with the assistance of an oscillating saw. The cotyle is prepared to receive the acetabular component composed of the cotyloidal cupule. The medullary cavity is adjusted by phantom rasps of the implant and filled with the previously prepared biological cement. The tail of the prosthesis is also coated with cement and its implanting is made with a moderate friction. The criteria of Merle d'Aubigné applied to the above-cited example show the excellence of the result of the use of the product according to the invention in the powdery form: indolence, stability of the unipodal bearing.

The radiological test carried out one year later shows an ossification of the biological cement prepared from the product according to the invention without any radioclear image between the pivot of the implant and the neoformed bone in the medullary cavity, giving evidence of an unquestionable stability of the prosthesis. It should be noted that the phenomena of mineralization of the paste formed of the product according to the invention and of the blood of the patient appear as from the first weeks and the formation of the neoformed bony tissue is complete one year later.

Another mode of utilization of the product according to the invention is illustrated by the example hereinbelow.

One knows that upon the provision of a vertebral arthrodesis, the autogenic graft is taken from the iliac crest sometimes affecting the internal and external lips as well as the internal and external faces of the upper portion of the iliac wing, thereby representing a substantial loss of substance aggravated by the possibility of a necrosis due to the lesion of a nutritious artery in the zone of the graft. In the example studied, the taking of the graft has caused a 60 mm long and 45 mm high bony defect accompanied by pains and by a functional helplessness through desinsertions of certain bundles of the musculus rectus abdominis, of the musculus transversus, of the musculus obliquus minor and of the superficial bundles of the musculus gluteus minimum. One fragment of the material according to the invention is cut to the dimensions of the loss of substance with a shoulder on the periphery bored through with holes for the insertion of the tendons of the desinserted muscles and the fastening onto the iliac wing.

The orthopaedic piece after treatment, decontamination and sterilization with a gamma radiation at 2.5 mgrd is inserted in such a manner that the pressure of the viscera presses it upon the iliac wing, fastened by means of screws cut in the material according to the invention. The bundles of the muscles and aponeuroses are reinserted by means of non resorbable ligatures.

The operative after-effects are normal. The clinical test shows a perfect reinsertion of the muscular bundles, the radiological test shows a perfect osteointegration of the material according to the invention without any inflammatory or immunological rejection phenomena.

These observations and experimentations show a) that the product according to the invention is perfectly biocompatible whatever its form might be b) that it results in no systemic rejection phenomenon during its utilization ;

c) that the treatment of the product according to the invention imparts thereto new functional qualities which extend its field of application ;

d) that the product according to the invention in powdery or plastic form exhibits adhesive, hemostatic properties.

We claim:

1. A semi-synthetic product intended to provide shaped pieces used in orthopaedic surgery, for bony regeneration and stabilization material, or biological sealing cement comprising modified mother of pearl of aquatic mollusca which has been subjected to a modification treatment comprising the steps of:

dipping mother of pearl into a first solution of demineralized water containing 20% of hypochlorite and boiling the solution for 2 hours, dipping the mother of pearl into a second solution of demineralized water containing 20% of hypochlorite and boiling the second solution for 2 hours, contacting the mother of pearl with demineralized water steam admixed with sodium hypochlorite, acetic acid, benzalkonium chloride or formaldehyde, diluted at 20% under a pressure of 2 bars for two periods of 2 hours, contacting the mother of pearl with demineralized water steam alone under a pressure of 2 bars for one hour, and drying under vacuum by thermal stages up to 100° C.

2. The product according to claim 1, which is made from the mother of pearl of Pinctada Maxima, of Pinctada Margaritifera, of Tricdane, of Concha, of Whelk, of Triton shell, of Nautilus, of Ormers.

3. The product according to claim 1 which is reduced to a powdery state with a granulometry extending from 1 to 100 microns.

4. The product according to claim 1 which is mixed in powdery form with calcium hydroxide, calcium phosphate, calcium chloride or any other calcium salt.

5. The product according to claim 1 which is in powdery form associated with collagen of animal or human origin, with starch in an extemporaneous manner.

6. The product according to claim 1 to be used when it is associated in powdery form with collagen of animal or human origin, with starch and then dried and molded in the shape of prosthetic elements usable in surgery.

7. The product according to claim 1 which is associated with monomers or polymers as well as with methylic or acrylic derivatives, antibiotic or antimitotic substances.

8. The utilization of the product according to claim 1 for the provision of implants, of shaped pieces in orthopaedic surgery, of osteotomy wedges, of intersomatic blocks, of screws and plates for osteosynthesis, of a support for the graft of the crystalline lens, of a birth control coil, of a substitute for the chain of ossicles of the middle ear.

9. A utilization of the product according to claim 1 in orthopaedic surgery, odontostomatology, and carcinological surgery.

* * * * *